(12) United States Patent
Hall

(10) Patent No.: US 8,771,361 B2
(45) Date of Patent: Jul. 8, 2014

(54) ARRANGEMENT FOR INCREASING THE STRESS RESISTANCE OF IMPLANTS AND ONE SUCH IMPLANT

(75) Inventor: Jan Hall, Gothenburg (SE)

(73) Assignee: Nobel Biocare Services AG, Kloten (CH)

( * ) Notice: Subject to any disclaimer, the term of this patent is extended or adjusted under 35 U.S.C. 154(b) by 405 days.

(21) Appl. No.: 12/236,903

(22) Filed: Sep. 24, 2008

(65) Prior Publication Data

US 2009/0024220 A1 Jan. 22, 2009

Related U.S. Application Data

(62) Division of application No. 10/521,149, filed as application No. PCT/SE03/01110 on Jun. 26, 2003, now abandoned.

(30) Foreign Application Priority Data

Jul. 25, 2002 (SE) .................................... 0202319

(51) Int. Cl.
*A61C 8/00* (2006.01)
(52) U.S. Cl.
USPC .................... 623/17.17; 606/190; 433/173
(58) Field of Classification Search
USPC ............... 623/17.17; 433/173, 174, 225, 227, 433/229; 606/190, 191, 193, 199
See application file for complete search history.

(56) References Cited

U.S. PATENT DOCUMENTS

| | | | | |
|---|---|---|---|---|
| 3,855,638 A | * | 12/1974 | Pilliar | 623/23.55 |
| 4,531,916 A | * | 7/1985 | Scantlebury et al. | 433/173 |
| 5,839,899 A | | 11/1998 | Robinson | |
| 5,899,696 A | * | 5/1999 | Shimoda | 433/173 |
| 6,299,448 B1 | * | 10/2001 | Zdrahala et al. | 433/173 |

FOREIGN PATENT DOCUMENTS

| | | |
|---|---|---|
| EP | 0748616 | 12/1996 |
| EP | 0832619 A1 | 4/1998 |
| JP | 8182690 | 7/1996 |
| WO | WO-0072775 | 12/2000 |
| WO | WO-0072776 | 12/2000 |
| WO | WO-0072777 | 12/2000 |

OTHER PUBLICATIONS

International Search Report of Appln. No. PCT/SE2003/01110 dated Oct. 7, 2003.

\* cited by examiner

*Primary Examiner* — Thomas J Sweet
*Assistant Examiner* — Christopher D Prone
(74) *Attorney, Agent, or Firm* — Walter Ottesen P.A.

(57) ABSTRACT

An arrangement and an implant are provided for increasing the stress resistance of the implant arranged in an upper jaw bone. The implant has access via parts to the sinus cavity. At said parts, the implant is arranged with a convex or rounded front surface which, upon access, lifts the sinus mucous membrane, without piercing the latter, and thus forms a closed space between the parts and the underside of the mucous membrane. The implant is provided, at least at said parts, with growth-stimulating substance or substances which interact with cell-containing body fluid which penetrates or has penetrated into the space, so that new bone is formed around said parts of the implant.

14 Claims, 2 Drawing Sheets

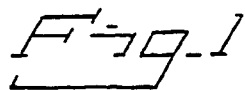
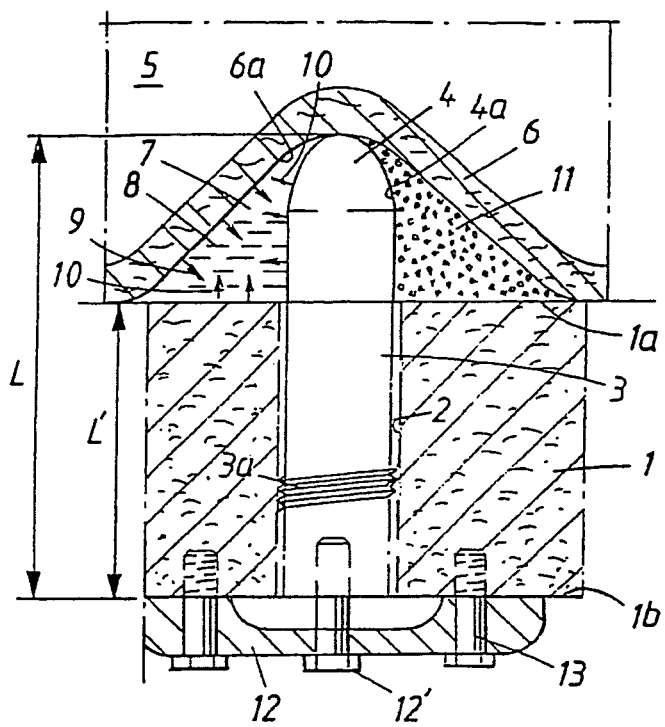
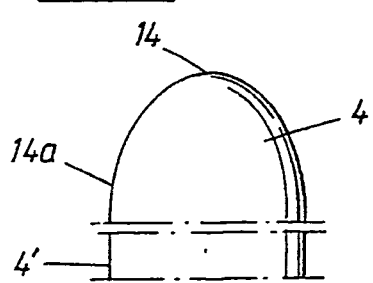
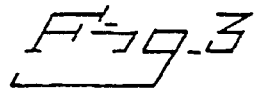
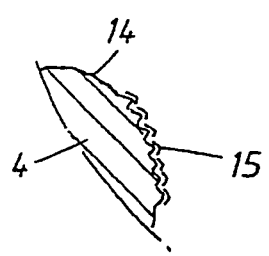
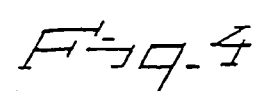
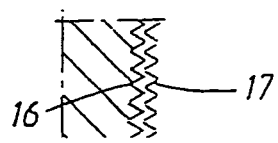

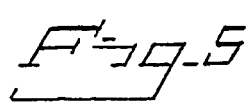 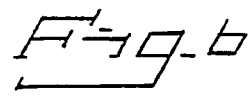
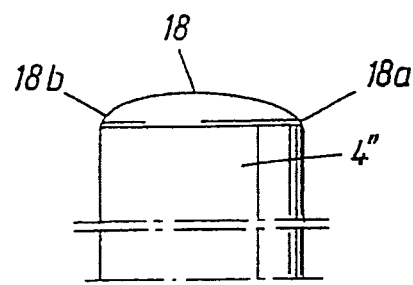 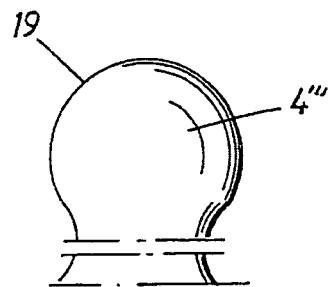
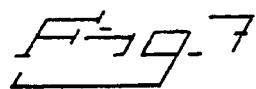
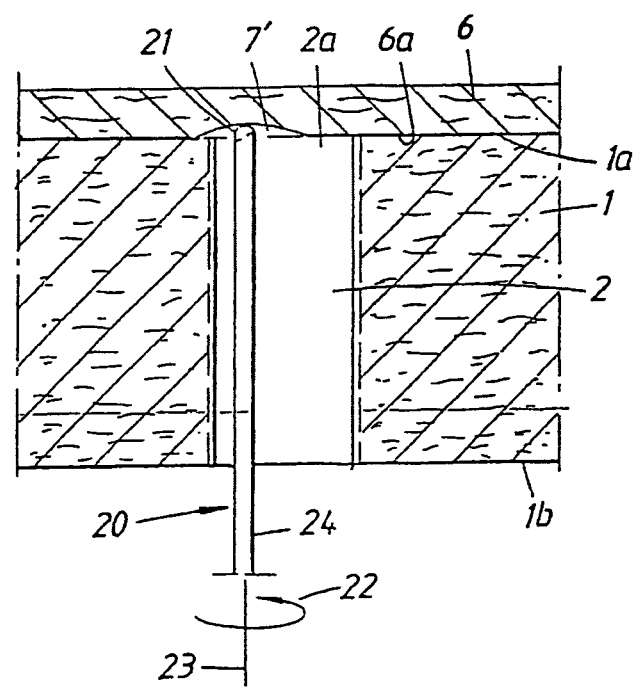

ARRANGEMENT FOR INCREASING THE STRESS RESISTANCE OF IMPLANTS AND ONE SUCH IMPLANT

This application is a divisional of application Ser. No. 10/521,149 filed Jan. 13, 2005, which is a national stage of PCT/SE03/01110 filed Jun. 26, 2003, claiming priority from Swedish application number 0202319-0 filed Jul. 25, 2002, the entire disclosures of which are herein incorporated by reference in their entireties.

The present invention relates to an arrangement for increasing the stress resistance of implants arranged in an upper jaw bone. The invention moreover relates to an implant for this purpose and made of titanium or of another biocompatible material, for example ceramic.

In connection with implants, there is a need to be able to increase the implant's stability in the jaw bone so that the implant does not collapse after having been exposed for some time to stresses which arise, for example, during chewing movements. It is known, in this connection, that the stability can be increased by means of the length of the implant being increased, i.e. the implant being anchored in a greater mass of jaw bone.

The present invention starts out from this understanding and proposes an arrangement and implants permitting this increase in length, which means that patients who for various reasons, for example poor upper jaw status, have hitherto been able to be provided with implants only of short lengths, for example implant lengths of 7-8 mm, can now be provided with implants having greater lengths, for example 10 mm or more. With the previously known technique, patients even had to do without the implant fixtures in question, due to the fact that the lengths which could be used on the patients were too short. The invention solves these problems, among others, and allows the implant length to be increased in relation to what was previously possible, and more independently of, for example, the upper jaw status.

The feature which can principally be regarded as characterizing an arrangement according to the invention is, inter alia, that the implant has a length which requires that the implant must be given access at parts to the sinus cavity and that the implant, at said parts, is arranged with a convex or rounded front surface which, upon access, lifts the sinus mucous membrane, without piercing the latter, and thus forms a closed space between the parts and the underside of the mucous membrane. The implant is provided, at least at said parts, with growth-stimulating substances which interact with cell-containing body fluid which has penetrated into the space, so that new bone is formed around said parts of the implant and thereby effects said resistance.

In a preferred embodiment, the convex or rounded front surface and at least one contiguous outer surface of the implant situated in the sinus are coated with layers of growth-stimulating substances. Said contiguous outer surface, and possibly at least parts of the front surface, are arranged with a rough outer layer or porous outer oxide layer(s) functioning as a reservoir for said growth-stimulating substance or substances. The roughness on the front surface is in this case designed not to cause penetration through the mucous membrane.

In one embodiment, the implant can be made of titanium and can be coated with growth-stimulating substance or substances, here called GSS, along most of its length. The growth-stimulating substance or substances can be matrix molecules, growth factors and differentiation factors and/or peptides with growth-stimulating properties. Other types of GSS can also be used. The implant can also be arranged in an upper jaw bone with reduced height, and the anchoring of the implant in the initial stage can in this case be complemented by mechanical anchoring elements, for example stiff membranes, which can be connected to the outer surface of the upper jaw bone. After incorporation, the anchoring is dependent on the degree of insertion of the implant in the sinus. The greater the degree of insertion, the greater the enclosed space, which means that the interacting body fluids and substances effect a greater formation of new bone around the implant.

The arrangement also comprises a member which can be introduced into a jaw bone hole extending from the outside of the jaw bone and opening into the sinus on the underside of the sinus mucous membrane. In the inserted position below said underside, the member is designed to effect a rotation movement as a function of a turning action, preferably of a manual type. The member has one or more front parts which are designed to be able to pass in between the boundary wall of the sinus and the underside of the mucous membrane and, upon said rotation movement or rotation movements, to free parts of the mucous membrane from the boundary wall of the sinus.

An implant according to the invention is characterized principally in that it is arranged with a convex or rounded front surface which can cooperate with the mucous membrane in the sinus, via the underside of the mucous membrane, to form an enclosed space between the implant and the underside of the mucous membrane. At least the parts which penetrate or have penetrated into the sinus are coated with growth-stimulating substance or substances arranged to interact with cell-containing body fluid in said enclosed space in order to form new bone around the front surface and the parts.

In a preferred embodiment, the parts of the implant on the outside in the sinus are designed with a roughened outer surface or porous outer oxide layer arranged to store said substance or substances.

By means of what has been proposed above, growth-stimulating substance or substances (GSS) can be used effectively, and examples of GSS which may be mentioned are matrix molecules, growth factors and differentiation factors and/or peptides with growth-stimulating properties. In accordance with the invention, the mucous membrane must be protected against mechanical action, and this is achieved effectively by the proposed lifting function, in possible combination with the release function between the mucous membrane and the wall of the sinus. By means of what is proposed, it is possible to create an effectively enclosed space in which the cell-containing fluid can gain access and effectively interact with the GSS which is released from the implant.

A presently proposed embodiment of an arrangement and of an implant according to the invention will be described below with reference to the attached drawings, where FIG. 1 shows, in vertical section, an implant which is fitted in a hole in the upper jaw bone and whose front parts have passed into the sinus and cooperate with the mucous membrane, at the underside thereof, so that a closed space for production of new bone is created, FIG. 2 shows, in a vertical view, and enlarged in relation to FIG. 1, the configuration of the front surface of the implant and parts penetrating into the sinus, FIG. 3 shows, in vertical section, and enlarged in relation to FIG. 2, parts of the front surface with applied growth-stimulating substance or substances, FIG. 4 shows, in vertical section, other parts of the implant's side surfaces which are coated with layers of growth-stimulating substance or substances, which outer sides can comprise one or more threads, FIG. 5 shows, in a vertical view, a second embodiment of the front surface of the implant, FIG. 6 shows, in vertical view, a third embodiment of the front surface of the implant, and FIG. 7 shows, in vertical section, members or instruments which, before lifting of the mucous membrane of the sinus, are intended to free the latter from the inner surface of the sinus.

In FIG. 1, an upper jaw bone is represented by 1. A hole 2 with an internal thread has been formed in the jaw bone. An implant 3 has been fitted in the hole in the jaw bone, its front parts 4 passing into a sinus 5. The insertion in this case is such that the front parts 4 have lifted the mucous membrane 6 of the sinus by means of the implant's front parts 4 cooperating with the mucous membrane at the underside 6a thereof. It is important here that the lifting is done in such a way that the mucous membrane 6 is not pierced by the implant or is not damaged in a way which would involve a risk of its later becoming pierced. The lifting of the mucous membrane 6 results in an enclosed space 7 being formed between the underside 6a of the mucous membrane and the outer surface 4a of the outer parts. Body fluid 8 passes into the enclosed space from the body tissue in accordance with arrows 9 and 10. At least said front parts 4 of the implant are provided, on said outer surface 4a, with growth-stimulating substance or substances which interact with said body fluid 8. The substance or substances are initially applied in a specific amount and concentration on said surface 4a, and said interaction from said layer is represented in the figure by arrows 10. In FIG. 1, the formation of new bone has been symbolized by 11. Two stages have been indicated in the figure. In the first stage (see to the left of the front surface 4a), the body fluid accumulation and the initial interaction are indicated. In the second stage (see to the right of the front parts 4), the completed formation of new bone is indicated. The figure also shows an inner surface 1a of the upper jaw bone, against which inner surface the underside 6a of the mucous membrane 6 bears before lifting. The implant can be of the self-tapping type or of the type fitted in a previously formed thread in the jaw bone hole 2. In FIG. 1, parts of an outer thread on the implant 3 have been indicated by 3a. Other parts of the implant can also be provided with amounts or concentrations of growth-stimulating substance or substances lying on the outside. Application of GSS to the implant 3 can be carried out in different ways, and with variations as regards the extent of the substance or substances along the length and circumference of the implant. The implant has a length L in accordance with the above. The height or length L' of the dentine can vary as a function of the patient, jaw bone status, etc. The degree of insertion of the implant, i.e. L-L', is dependent inter alia on the length or height L'. If the length or height is small, it may be important to increase stability by means of the new bone formation in the closed space 7, which in such a case entails a greater degree of insertion of the front parts 4 of the implant. The implant can be anchored to the jaw bone 1 temporarily or permanently using a mechanical securing arrangement 12, for example a stiff membrane, which is secured with screws 13 in the jaw bone, at the outer surface 1b thereof.

Alternatively, or in addition to this, the membrane or reinforcement can be secured by a screw 12' which is screwed into an inner threaded hole in the implant. The design of the implant itself can be of a type known per se, and in this connection reference may be made to the "Brånemark" system.

FIG. 2 is an enlarged view showing the configuration of the front surface 4a in FIG. 1. The front surface is designed with an evenness which avoids mechanical impact on the mucous membrane when the implant is inserted into the sinus. The front surface can have a polished part 14 and, if appropriate, can be designed with a surface roughness or porous layer 14a at the sides. The surface roughness or porous layer in this case functions as a reservoir for layers of GSS. The parts 4' contiguous to the front surface 4a can also be provided with said surface roughness or porous layer and can be charged with said GSS.

FIG. 3 shows the surface roughness 14 on the front surface 4a in an enlarged view compared to FIG. 2. A layer of GSS applied to the surface roughness is indicated by 15.

In accordance with the above, the rest of the implant 3 can be coated completely or partially with GSS of a chosen amount and concentration 17. The thickness of the applied GSS can, for example, lie in the range of, for example, a few Angstrom to a few micrometers, a few nanometers. In the example according to FIG. 4, a coating has been applied to an outer thread 16 with a GSS amount or GSS concentration 17. In the figures, the GSS has been symbolized by broken lines 15 and 17.

In accordance with FIG. 5, the front surface 4" can be designed in different ways. The front surface can be substantially planar or form an only slightly rounded front surface 18 which, at its periphery, has been provided with bevels 18a, 18b so as not to cause damage to the aforementioned mucous membrane 6.

FIG. 6 shows a further embodiment of the front surface 4''', which in this case has the basic shape of a sphere 19.

In accordance with FIG. 7, the mucous membrane 6 can, at its underside 6a, be more or less firmly attached to or in the inner surface 1a of the upper jaw bone 1. In this case it is advantageous to use a certain release function. The purpose of the release function is to free the mucous membrane 6 from the inner surface 1a before the lifting in accordance with FIG. 1 is carried out. Said release can be done with the aid of an instrument or member 20 which at its front part has a blade-shaped part 21. After passing through the jaw bone hole 2, said part 21 can be driven in between the inner surface 1a of the jaw bone and the underside 6a of the mucous membrane 6 so as to effect a release function between the jaw bone and the mucous membrane. FIG. 7 shows this initial stage. The member 20 can be given a rotation movement 22 about its longitudinal axis 23, which results in the mucous membrane 6 being freed from the inner surface 1a around the mouth 2a where the jaw bone hole opens into the sinus. In FIG. 7, an initial stage for formation of the space 7 in FIG. 1 has commenced. The initial space which has been created with the member 20 in the stage shown in FIG. 7 has been indicated by 7'. It will be appreciated that the member 20 and its insertion and releasing parts 21 can be designed in different ways. Thus, the member 20 can be provided with several parts 21. The parts can be arranged to be resilient relative to the longitudinal part 24 of the member. The part or parts 21 can be provided with rounded surfaces cooperating with the mucous membrane 6 so that the latter is not damaged by the member 20 during the initial release. The invention has been described above such that the mucous membrane 6 is considered as belonging to the sinus, like any space between the underside 6a of the mucous membrane and the top surface 1a of the jaw bone.

The invention is not limited to the embodiment shown above by way of example, and instead it can be modified within the scope of the attached patent claims and the inventive concept.

Reference may be made here to patent applications submitted to the Swedish patent office on the same day as the present patent application and by the same Applicant and inventor. Said applications have the following titles:
a) "Arrangement for using osteoinductive or bioactive material to induce bone and/or increase the stability of implants in the jaw bone, and an implant intended for this purpose".
b) "Arrangement for using bioactive or osteoinductive material to build up a bone-based lateral support for implants in the jaw bone".
c) "Arrangement for implants bearing growth-stimulating substance or substances, and one such implant".
d) "Arrangement of two or more implants provided with growth-stimulating substance(s)".

The invention claimed is:

1. A method of using an implant in a sinus cavity of a patient comprising:
    obtaining an implant having a length, an outer surface at least partially coated with a growth stimulating substance (GSS), and a rounded front part having a polished part and configured to pass through an upper jaw bone of the patient and to push but not pierce a mucous membrane adjacent the sinus;
    forming a hole in the upper jaw bone adjacent the sinus cavity of the patient;
    inserting the implant through the formed jaw bone hole such that the partially coated portion of the outer surface extends beyond the formed hole and into the sinus cavity;
    pushing the mucous membrane of the sinus cavity with the rounded front part of the implant so as to lift the mucous membrane from a surface of the upper jaw bone and to form a space between the surface of the upper jaw bone and the pushed mucous membrane; and
    allowing the GSS to be released from the partially coated portion of the outer surface of the implant and to interact with fluids deposited in the space so as to form new bone in the space;
    wherein the rounded front part has a front surface and the front surface comprises the polished part and is designed with a surface roughness or porous layer at sides thereof, and the surface roughness or porous layer functions as a reservoir for layers of GSS.

2. The method of claim 1, further comprising:
    securing the implant to the upper jaw bone after said inserting the implant through the jaw bone hole.

3. The method of claim 2, wherein the implant further comprises an anchor configured for said securing the implant to the upper jaw bone.

4. The method of claim 1, wherein the GSS released from the partially coated portion of the outer surface of the implant is at least one member selected from the group consisting of matrix molecules, growth factors, differentiation factors, and growth-stimulation peptides.

5. The method of claim 1, wherein at least a portion of the outer surface of the implant is porous and configured to store the GSS therein.

6. The method of claim 5, wherein porous outer surface of the implant comprises a porous oxide layer.

7. The method of claim 1, further comprising:
    separating the mucous membrane from the surface of the upper jaw bone prior to said pushing the mucous membrane with the front part of the implant.

8. The method of claim 7, wherein said separating the mucous membrane from the surface of the upper jaw bone comprises:
    inserting a membrane separation instrument through the jaw bone hole and adjacent to the mucous membrane; and
    rotating the membrane separation instrument in its inserted position so as to separate the mucous membrane from the surface of the upper jaw bone.

9. The method according to claim 1, further comprising depositing the fluids in said space.

10. The method according to claim 1, wherein the implant further comprises one or more outer threads, and wherein the GSS is only at a side of a tip of the implant.

11. The method according to claim 10, further comprising: securing the implant to the upper jaw bone after said inserting the implant through the jaw bone hole, wherein the implant further comprises an anchor configured for said securing the implant to the upper jaw bone, and wherein said securing comprises: securing the anchor in the upper jaw bone with screws.

12. The method according to claim 11, wherein the securing of the implant to the upper jaw bone comprises securing the anchor with the screw, which is screwed into an inner threaded hole of the implant.

13. The method according to claim 1, wherein the implant further comprises one or more outer threads.

14. The method according to claim 1, wherein the GSS is only at a side of a tip of the implant.

* * * * *

UNITED STATES PATENT AND TRADEMARK OFFICE
CERTIFICATE OF CORRECTION

| | | |
|---|---|---|
| PATENT NO. | : 8,771,361 B2 | Page 1 of 1 |
| APPLICATION NO. | : 12/236903 | |
| DATED | : July 8, 2014 | |
| INVENTOR(S) | : Jan Hall | |

It is certified that error appears in the above-identified patent and that said Letters Patent is hereby corrected as shown below:

On the Title page, under Related U.S. Application Data, at Item (62), please insert after "filed": -- on Jan. 13, 2005, now abandoned, which is a national stage of application No. PCT/SE03/01110, filed on Jun. 26, 2003. -- and delete "as application No. PCT/SE03/01110 on Jun. 26, 2003, now abandoned".

In the Claims

In Column 6:
Line 9: please insert -- the -- before "porous".

Signed and Sealed this
Fourteenth Day of October, 2014

Michelle K. Lee
*Deputy Director of the United States Patent and Trademark Office*